(12) United States Patent
Sakai et al.

(10) Patent No.: US 6,524,796 B1
(45) Date of Patent: Feb. 25, 2003

(54) HUMAN P27$^{KIP1}$ GENE PROMOTER

(75) Inventors: Toshiyuki Sakai; Naoko Ohtani, both of Kyoto (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 09/491,971

(22) Filed: Jan. 27, 2000

Related U.S. Application Data

(62) Division of application No. 09/103,510, filed on Jun. 23, 1998, now Pat. No. 6,225,112.

(30) Foreign Application Priority Data

Nov. 7, 1997 (JP) .............................................. 9-305196

(51) Int. Cl.$^7$ ......................... C12N 15/63; C07K 13/00; C07H 21/04
(52) U.S. Cl. ........................... 435/6; 530/350; 536/23.1
(58) Field of Search ........................ 435/6, 320.1, 455; 536/23.1, 24.1

(56) References Cited

U.S. PATENT DOCUMENTS 5,807,740 A * 9/1998 Amaral et al. ............... 435/325
6,048,693 A    4/2000 Bitter

OTHER PUBLICATIONS

Kwon et al. Characterization of the murine cyclin–dependent kinase inhibitor gene p27kip1. Gene vol. 180:113–120, 1996.*

Akiyama et al., "G$_1$ Phase Accumulation Induced by UCN–01 Is Associated with Dephosphorylation of Rb and CDK2 Proteins as well as Induction of CDK Inhibitor p21/Cip1/WAF1/Sdi1 in p53–Mutated Human Epidermoid Carcinoma A431 Cells," *Cancer Research* 57:1495–1501 (1997).

Datto et al., "Functional Analysis of the Transforming Growth Factor β Responsive Elements in the WAF1/Cip1/p21 Promoter," *J. Biol. Chem.*, 270:28623–28628 (1995).

Liu et al., "Transcriptional Activation of the Cdk Inhibitor p21 by Vitamin D$_3$ Leads to the Induced Differentiation of the Myelomonocytic Cell Line U937," *Genes & Development* 10:142–153 (1996).

Kwon et al. Characterization of the murine cyclin–dependent kinase inhibitor gene p27kip1. Gene. vol. 180:113–120., Jul., 1996.*

Zhang et al. Molecular characterization of the cyclin–dependent kinase inhibitor p27 promoter. Bioch. Biophys. Acta. vol. 1353:307–317. Apr. 1997.*

Mimami et al. Molecular cloning and characterization of the human p27kip1 gene promoter. FEBS Lett. vol. 411:1–6. Jul. 1997.*

Minami et al., "Molecular Cloning and Characterization of the Human p27$^{Kip1}$ Gene Promoter," *FEBS Letters* 411:1–6 (1997).

Toyoshima et al., "p27, A Novel Inhibitor of G1 Cyclin–Cdk Protein Kinase Activity, Is Related to p21," *Cell.* 78:67–74 (1994).

Zhang et al., "Molecular Characterization of the Cyclin–Dependent Kinase Inhibitor p27 Promoter," *Biochim. Biophys. Acta* 1353:307–317 (1997).

* cited by examiner

*Primary Examiner*—Terry McKelvey
*Assistant Examiner*—William Sandals
(74) *Attorney, Agent, or Firm*—Clark & Elbing LLP

(57) ABSTRACT

The promoter of the human p27$^{Kip1}$ gene is provided. The promoter region is useful to screen a compound that regulates the promoter of the human p27$^{Kip1}$ gene or regulates the activity of the promoter. It enables the gene therapy utilizing the promoter.

1 Claim, 5 Drawing Sheets

```
CCACGGTGCTCAAGCCCACACTGAGAGAGAAATTTCCAGCTGCAAAAGGGAGAAGAGAAACG
                                 -1600
CTGGAATACTAGTATCGGACGTTAGGACATGGTTGTGGTGTTTTAAAAATCATTTCATCATC

TGGAGTTTGACCCCGAGGGGAGTATTTTCACCCTTCAGCCCTCTGAAAGCATTCACTAGCAT
                     -1500
CTGAATATTGTTCTGAGTTTGTTGGAGCAGTGAAATCTGGTGAGAGAGAAGGGTGGAGGAAG
                                                       PEA3 1400
GAAGGAGCTGTTGTATTTGGCGGCTGGACTCAGGTAGAGGAAACTGCTACAATCCCGGGAAA
PEA3
GAACAGAAAAGTAGAAAGGGACGAGTTCCCACACGCAGCCAATGTCCATGGCCTTAACTGTG
                                    -1300  CTF             Myb
CTTGGGAAGGAAGATCCTGGGCCAGGGGTGTACCCTCGTTTTTCAAAAACTAAACGTGTCTG
       PEA3
AGACAGCTACAAAGTTTATTAAGGGACTTGAGAGACTAGAGTTTTTTGTTTTTTTTTTTTAA
         -1200
TCTTGAGTTCCTTTCTTATTTTCATTGAGGGAGAGCTTGAGTTCATGATAAGTGCCGCGTCT
                                                         -1100
ACTCCTGGCTAATTTCTAAAAGAAAGACGTTCGCTTTGGCTTCTTCCCTAGGCCCCCAGCCT

CCCCAGGGATGGCAGAAACTTCTGGGTTAAGGCTGAGCGAACCATTGCCCACTGCCTCCACC
                  -1000
AGCCCCCAGCAAAGGCACGCCGGCGGGGGGGCGCCCAGCCCCCCCAGCAAACGCTCCGCGGC

CTCCCCCGCAGACCACGAGGTGGGGGCCGCTGGGGAGGGCCGAGCTGGGGGCAGCTCGCCAC
 -900                                                     AP2
CCCGGCTCCTAGCGAGCTGCCGGCGACCTTCGCGGTCCTCTGGTCCAGGTCCCGGCTTCCCG
                              -800
GGAGAGGAGCGGGAGGGAGGTCGGGGCTTAGGCGCCGCTGCGAACCCGCCAACGCAGCGCCG
     ┌─p27Apa I                                      AP2
GGCCCCGAACCTCAGGCCCCGCCCCAGGTTCCCGGCCGTTTGGCTAGTTTGTTTGTCTTAAT
            -700 Sp1 AP2
TTTAATTTCTCCGAGGCCAGCCAGAGCAGGTTTGTTGGCAGCAGTACCCCTCCAGCAGTCAC
                                                          -600
GCGACCAGCCAATCTCCCGGCGGCGCTCGGGGAGGCGGCGCGCTCGGGAACGAGGGGAGGTG
         CTF
GCGGAACCGCGCCGGGGCCACCTTAAGGCCGCGCTCGCCAGCCTCGGCGGGGCGGCTCCCGC
                    -500                                Sp1   Sp1
CGCCGCAACCAATGGATCTCCTCCTCTGTTTAAATAGACTCGCCGTGTCAATCATTTTCTTC
         CTF              ┌─p27MB-435
TTCGTCAGCCTCCCTTCCACCGCCATATTGGGCCACTAAAAAAGGGGGCTCGTCTTTTCGG
  ATF -400
GGTGTTTTTCTCCCCCTCCCCTGTCCCCGCTTGCTCACGGCTCTGCGACTCCGACGCCGGCA
         AP2                   ┌─p27Sac II -300
AGGTTTGGAGAGCGGCTGGGTTCGCGGGACCGCGGGCTTGCACCCGCCCAGACTCGGACGGG
                              PEBP2 AP2        Sp1
CTTTGCCACCCTCTCCGCTTGCCTGGTCCCCTCTCCTCTCCGCCCTCCCGCTCGCCAGTCCA
        -200                                 Sp1    AP2  ┌─p27BssH II
TTTGATCAGCGGAGACTCGGCGGCCGGGCCGGGGCTTCCCCGCAGCCCCTGCGCGCTCCTAG
▼                                  NFκB                       -100
AGCTCGGGCCGTGGCTCGTCGGGGTCTGTGTCTTTTGGCTCCGAGGGCAGTCGCTGGGCTTC

CGAGAGGGGGTTCGGGCCGCGTAGGGGCGCTTTGTTTTGTTCGGTTTTGTTTTTTTGAGAGT
                                  1
GCGAGAGAGGCGGTCGTGCAGACCCGGGAGAAAGATG
```

Fig. 1

```
-811 CCTAGATCCCCGGGTCCCTGCCTGGCCGCCGCGCTGGCCCCTCCCCAGCTCTCCGGCCGT mo
       *   *  *  *****       ***   *  *  ******  ******  *  ********
-789 AC-GCAGCGCCGGG---------CCCCGAACCTCAGGCCCCGCCCCAGGTTCCCGGCCGT hu
                                        Sp1   AP2
-751 TTCGTGAGTTTGTTTGTCTTATTTTTAATTTCTCAGGGGCCAGCCAGAGCAGGTTTGTTG mo
     **  *  **************  ***********  *  ************************
-739 TTGGCTAGTTTGTTTGTCTTAATTTTAATTTCTCCGAGGCCAGCCAGAGCAGGTTTGTTG hu

-691 GCAGTCGTACACCTCCGAGTAGTCACGCGACCAGCCAATGTCCTGGCGGCGCTACGGGGA mo
     ****  ****  *****  **  ******************  ***  *********  ******
-679 GCAGCAGTACCCCTCC-AGCAGTCACGCGACCAGCCAATCTCCCGGCGGCGCT-CGGGGA hu
                                          CTF

-631 GGCGGC-CGCTCGGGAGCCAGAGGCGGCGGCGG--CC----CGGGGCCACCTTAAGAGCG mo
     ******  ************  *  **  **  *****   **   **************  **
-621 GGCGGCGCGCTCGGGAACGAGGGGAGGTGGCGGAACCGCGCCGGGGCCACCTTAAGGCCG hu

-578 CG-TCG-CAGCCT----GGGGAGGCTCCCGGCACCGAGACCAATGGAGCTCCTCCTCTGT mo
     **  ***  ******      ****  ********  *  ***   *********  ***********
-561 CGCTCGCCAGCCTCGGCGGGGCGGCTCCCGCCGCCGCAACCAATGGATCTCCTCCTCTG- hu
                     Sp1     Sp1            CTF
-524 TTTAAATAGACTTGCAGTGTCAATCATCTTCTTCGTCAGCCTCCCTTCCACCGCCAT mo
     ***********  **  ***********  ********************************
-502 TTTAAATAGACTCGCCGTGTCAATCATTTTCTTCTCGTCAGCCTCCCTTCCACCGCCAT hu
                                        ATF
-464 ATTGGGCAACTAAAAAAGGAGGGGGGCTGCTTT-TGGGTGTTTTCCCCCTCGTCCCTTGT mo
     *******  ********  *  ***    *   ***  ********  *  **   ****  ***
-442 ATTGGGCCACTAAAAAAAGGGGGCTCGTCTTTTCGGGGTGTTTTTCTCCCCCTCCCCTGT hu
                                                        AP2
-405 -CCCACTCACTCGCGGCTCCGAGACT-GGGCGGCGGCAAGGTTTGGAGAGGGGCT-GGTT mo
      ***  **   ***  ******  *  ****  *  **  ****************  ****  ****
-382 CCCCGCTTGCTCACGGCTCTGCGACTCCGACGCCGGCAAGGTTTGGAGAGCGGCTGGGTT hu

-348 CGCGGGA-CACACGCTCGCCCCAGCCTACGCTCCGAC--TGTTTGCCA-CCT--CCTCCT mo
     *******  *  *    ***  **  **  ***   *   ***   ***   *******  ***  **  *  *
-322 CGCGGGACCGCGGGCTTGCACCCGCCCAGACTCGGACGGGCTTTGCCACCCTCTCCGCTT hu
          PEBP2  AP2           Sp1
-294 GCCTCCTCCCCTCCCTTCCCCGCCCTCCAGTACACTTGATCACTGAAGCCTCGAGCTGCG mo
     ****   *******  *  **  ********  *    *   *  **   *   **  *   *
-262 GCCTGGTCCCCTCTCCTCTCCGCCCTCCCGCTCGCCAGTCCATTTGATCAGCG-GAGACT hu
                      Sp1    AP2       ▽
-234 CGGCGGCTGGGGTGTCCCTGCGCCTCTCTTCCCCAGACCTGCGCGCTACTGCGGCTCGGG mo
     *******  ***  *     *  **  **   *   *  *  **********   **   *******
-203 CGGCGGCCGGGCCG-----GGGCTTCCCCGCAGC--CCCTGCGCGCTCCTAGAGCTCGGG hu
                     NFκB                                    ▲
-174 CGGTCGCTCGCCTGGCTCTGCTCCATTTGACTGTCTGTGTGCAGTCGCAGAACTTCGAAG mo
     *  **  *****  *  **  ****    *  ****  *  **   *  ********  *   ****  **
-150 CCGTGGCTCGTCGGGGTCTGTGTCTTTTGGC--TCCGAGGGCAGTCGCTGGGCTTCCGAG hu

-114 AGGGTTTTGCGCTCCATCCGTGGCG-TTTCGCTTTTGTTCGGTTTTGTTGTTTATTTC-A mo
     ****  **   *   *   *  ****                  ******   ***
 -92 AGGGGGTTCGGGCCGCGTAGGGGCGC------------------TTTGTTTTGTTCGG hu

-56 TTTTTTTTTTTCCGGAGAGAG-GCGAGGCGGTGGTCCACACCCGCCCGAGGAGGAAGATG mo
     ****  ******    ***  *  *   ********  **  **  *****        ***  ******
 -52 TTTTGTTTTTTTGAGAGTGCGAGAGAGGCGGTCGTGCAGACCCG-----GGAGAAAGATG hu
```

Fig. 5

HUMAN P27$^{KIP1}$ GENE PROMOTER

This application is a division of U.S. application No. 09/103,510, filed, Jun. 23, 1998 now U.S. Pat. No. 6,325,112.

FIELD OF THE INVENTION

The present invention relates to a promoter of human p27$^{Kip1}$ gene and to a method of screening a compound capable of regulating activity of the promoter.

BACKGROUND OF THE INVENTION

In the eukaryotic cell cycle, several positive and negative factors control the cell cycle progression. Among the positive factors, the protein kinase family plays an important role. Each member of the family comprises a regulatory subunit, or cyclin, and a catalytic subunit named cyclin-dependent kinase (cdk). A number of reports have suggested that cyclin D-cdk4, cyclin D-cdk6, and cyclin E-cdk2 play important roles in promoting the transition from the G1 phase to the S phase by the phosphorylation of retinoblastoma protein (pRB). Recently, one further level of control has become apparent, namely the expression of cdk inhibitors (Sherr, C. J. and Roberts, J. M. (1995) Genes & Dev. 9:1149–1163). Two families of cdk inhibitor with different modes of action have already been identified in mammalian cells. One group, comprised of related proteins known as p21$^{Cip1}$, p27$^{kip1}$, and p57$^{Kip2}$, appears to function as specific inhibitors of the cyclin/cdk complexes (Harper, J. W., Adami, G. R., Wei, N., Keyomarsi, K. and Elledge, S. J. (1993) Cell 75: 805–816; Polyak, K., Lee,M.-H., Erdjument-Bromage, H., Koff, A., Roberts, J. M., Tempst, P., and Massague, J. (1994) Cell 78: 59–66; Toyoshima, H. and Hunter, T. (1994) Cell 78: 67–74; Matsuoka, S., Edwards, M. C., Bai, C., Parker, S., Zhang, P., Baldini, A., Harper, J. W., and Elledge, S. J. (1995) Genes & Dev. 9: 650–662). The second family of the cdk inhibitors is called INK4 family proteins. The four members of this family, called p15, p16, p18, and p19, bind directly to cdk4 and cdk6, and are therefore specific inhibitors of the cyclin D-dependent kinases (Hannon, G. J. and Beach, D. (1994) Nature 371: 257–261; Serrano, M., Hannon, G. J., and Beach, D. (1993) Nature 366: 704–707, Hirai, H., Roussel, M. F., Kato, J., Ashmun, R. A., and Sherr, C. J. (1995) Mol. Cell. Biol. 15: 2672–2681).

Although the precise roles of p27$^{kip1}$ are far from clear, its level decreases when cells are stimulated to enter the cell cycle, and increases when cells are arrested by either the change in TGF-β concentration or contact inhibition (Polyak, K., Kato, J., Solomon, M. J., Sherr, C. J., Massague, J., Roberts, J. M., and Koff, A. (1994) Genes & Dev. 8: 9–22). p27$^{kip1}$ was cloned as a binding protein with cyclin E-cdk2 (Polyak, K., Lee, M.-H., Erdjument-Bromage, H., Koff, A., Roberts, J. M., Tempst, P., and Massague, J. (1994) Cell 78: 59–66) or cyclin D-cdk4 (Toyoshima, H. and Hunter, T. (1994) Cell 78: 67–74). p27$^{kip1}$ inhibits the activity of most cyclin-cdk complexes and can inhibit the phosphorylation of cyclin-cdk complexes by CAK (cdk-activation kinases) (Kato. J., Matsuoka, M., Polyak, K., Massague, J., and Sherr, C. J. (1994) Cell 79: 487–496). Therefore, p27$^{kip1}$ functions as a negative regulator of the G1/S progression.

Tumor-specific mutations of the p27$^{kip1}$ gene are rare, whereas several cell cycle regulators, such as p16, p53, and pRB, are frequently mutated in some cancers and have been shown to be tumor suppressor genes (Ponce-Castaneda, M. V., Lee, M.-H., Latres, E., Polyak, K., Lacombe, L., Montgomery, K., Mathew, S., Krauter, K., Sheinfeld, J., Massague, J., and Cordon-Cardo, C. (1995) Cancer Res. 55: 1211–1214). However, the p27$^{kip1}$-deficient mice were observed to have increased body size, multiple organ hyperplasia, retinal dysplasia, and formation of pituitary tumors (Fero, M. L., Rivkin, M., Tasch, M., Porter, P., Carow, C. E., Firpo, E., Polyak, K., Tsai, L.-H., Broudy, V., Perlmutter, R. M., Kaushansky, K., and Roberts, J. M. (1996) Cell 85: 733–744; Kiyokawa, H., Kineman, R. D., Manova-Todorova, K. O., Soares, V. C., Hoffman, E. S., Ono, M., Khanam, D., Hayday, A. C., Frohman, L. A., and Koff, A. (1996) Cell 85: 721–732; Nakayama, K., Ishida, N., Shirane, M., Inomata, A., Inoue, T., Shishido, N., Horii, I., Loh, D. Y., and Nakayama, K. (1996). Cell 85: 707–720). These data are in part similar to the case of the RB heterozygous knockout mice (Hu, N., Gutsmann, A., Herbert, D. C., Bradley, A., Lee, W.-H., and Lee, E. Y.-H. P. (1994) Oncogene 9:1021–1027). In addition, it has been shown that lower expression of the p27$^{kip1}$ protein correlated with poorer survival in breast cancer and colorectal cancer (Porter, P. L., Malone, K. E., Heagerty, P. J., Alexander, G. M., Gatti, L. A., Firpo, E. J., Daling, J. R., and Roberts, J. M. (1997) Nature Medicine 3: 222–225; Catzavelos, C., Bhattacharya, N., Ung, Y. C., Wilson, J. A., Roncari, L., Sandhu, C., Shaw, P., Yeger, H., Morava-Protzner, I., Kapsuta, L., Franssen, E., Pritchard, K. I., and Slingerland, J. M. (1997) Nature Medicine3: 227–230; Loda, M., Cukor, B., Tam, S. W., Lavin, P., Fiorentino, M., Draetta,.G. F., Jessup, J. M., and Pagano, M. (1997) Nature Medicine 3: 231–234). These results clearly indicate that p27$^{kip1}$ plays an important role in inhibiting tumor formation and tumor progression. There have also been reports on the importance of the p27$^{kip1}$ gene in enhancing the susceptibility of tumor cells to anticancer drugs and in influencing the prognosis factors of cancers (Croix, B. S., Florenes, V. A., Rak, J. W., Flanagan, M., Bhattacharya, N., Slingerland, J. M., and Kerbel, R. S. (1996) Nature Medicine 2: 1204–1210; Loda, M., Cukor, B., Tam, S. W., Lavin, P., Fiorentino, M., Draetta, G. F., Jessup, J. M., and Pagano, M. (1997) Nature Medicine 3: 231–234; Hengst, L. and Reed, S. I. (1996) Science 271: 1861–1864; Pagano, M., Tam, S. W., Theodoras, A. M., Beer-Romero, P., Sal, G. D., Chau, V., Yew, P. R., Draetta, G. F., and Rolfe, M. (1995) Science 269: 682–685). Consequently, it has been desired to develop drugs that regulate the transcription of the p27$_{Kip1}$ gene in order to prevent or treat malignant tumors.

Recent reports showed that p27$^{kip1}$ mRNA is induced by vitamin D3 in U937 cells (Liu, M., Lee, M.-H., Cohen, M., Bommakanti, M., and Freedman, L. P. (1996) Genes & Dev. 10: 142–153) and by neuronal differentiation (Poluha, W., Poluha, D. K., Chang, B., Crosbie, N. E., Schonhoff, C. M., Kilpatrick, D. L., and Ross, A. H. (1996) Mol. Cell., Biol. 16: 1335–1341). These facts suggest that the transcriptional regulation of the p27$^{kip1}$ gene might also be important in cellular differentiation.

SUMMARY OF THE INVENTION

An object of the present invention is to provide the promoter of the human p27$^{kip1}$ gene and a method of screening a compound capable of regulating the activity of the promoter.

The present inventors earnestly studied to achieve the above object. As a result, the inventors succeeded in isolating an upstream region of the human p27$^{kip1}$ gene by preparing a partial fragment of the p27$^{kip1}$ cDNA and screening a human leukocyte genomic library using this fragment as a probe. Furthermore, the inventors succeeded in identifying the basal promoter activity region within the upstream region by preparing deletion mutants of the upstream region and detecting their promoter activities. In addition, the inventors found that it is possible to screen compounds capable of regulating the promoter activity by using the isolated promoter region.

Namely, the present invention relates to a promoter region of the human $p27^{kip1}$ gene and a method of screening a compound using the promoter region. More specifically, the invention relates to:

(1) a DNA comprising at least part of the nucleotide sequence of SEQ ID NO:1;
(2) a DNA comprising at least part of the nucleotide sequence of SEQ ID NO:1 and having the promoter activity;
(3) a vector comprising the DNA of (2) above;
(4) a cell carrying the vector of (3) above;
(5) a method of screening a protein capable of regulating the promoter activity of the DNA of (2) above, which comprises the steps selected from:
   (a) steps of bringing a test sample into contact with the DNA of (2) above and selecting a protein that binds to the DNA of (2) above;
   (b) steps of introducing a test DNA into cells carrying a reporter gene fused downstream of the DNA of (2) above and selecting an expression product that regulates the reporter gene expression; and
   (c) steps of bringing a test sample into contact with cells carrying a reporter gene fused downstream of the DNA of (2) above and selecting a protein that regulates the reporter gene expression;
(6) a method of screening a DNA encoding a protein capable of regulating the promoter activity of the DNA of (2) above, which comprises the steps selected from:
   (a) steps of bringing an expression product of a test DNA into contact with the DNA of (2) above and selecting a DNA encoding a protein that binds to the DNA of (2) above;
   (b) steps of introducing a test DNA into cells carrying a reporter gene fused downstream of the DNA of (2) above and selecting a DNA encoding an expression product that regulates the reporter gene expression; and
   (c) steps of bringing an expression product of a test DNA into contact with cells carrying a reporter gene fused downstream of the DNA of (2) above and selecting a DNA encoding an expression product that regulates the reporter gene expression;
(7) a method of screening a compound capable of regulating the promoter activity of the DNA of (2) above, which comprises the steps selected from:
   (a) steps of bringing a test sample into contact with the DNA of (2) above in the presence of a test compound and selecting a compound that promotes or inhibits the binding between the DNA of (2) above and a protein in the test sample; and
   (c) steps of bringing a test compound into contact with cells carrying a reporter gene fused downstream of the DNA of (2) above and selecting a compound that regulates the reporter-gene expression;
(8) a protein capable of regulating the promoter activity of the DNA of (2) above;
(9) the protein of (8) above, which can be isolated by the method according to (5) above;
(10) a DNA encoding a protein that regulates the promoter activity of the DNA of (2) above;
(11) the DNA of (10) above, which can be isolated by the method according to (6) above;
(12) a compound capable of regulating the promoter activity of the DNA of (2) above; and
(13) the compound of (12) above, which can be isolated by the method according to (7) above.

BRIEF DESCRIPTION OF THE DRAWINGS

FIG. 1 shows the nucleotide sequence of the human $p27_{Kip1}$ gene 5' flanking region (SEQ ID NO:7). The transcriptional start site of the human $p27_{Kip1}$ gene was determined by primer extension, and is indicated by the solid triangle. The consensus sites for various transcription factors are underlined. The number of nucleotides was counted from the transcriptional start site. The arrowheads indicate the 5' termini of the $p27_{Kip1}$ promoter deletion mutants shown in FIG. 3.

FIG. 5 illustrates the homology between the human and the mouse $p27^{Kip1}$ promoter sequences. The DNA sequence of the human (indicated as "hu"; SEQ ID NO:8) was compared with that of the mouse (indicated as "mo"; SEQ ID NO:4) $p27^{Kip1}$ promoters using the GENETYX software. The presumed basal activity region from position −774 to position −435 is enclosed by the broken line. The transcriptional start sites for the human (solid triangle) and the mouse (open triangle) $p27^{Kip1}$ genes are indicated. Consensus sites for various transcription factors are underlined.

DETAILED DESCRIPTION OF THE INVENTION

Figure 2:
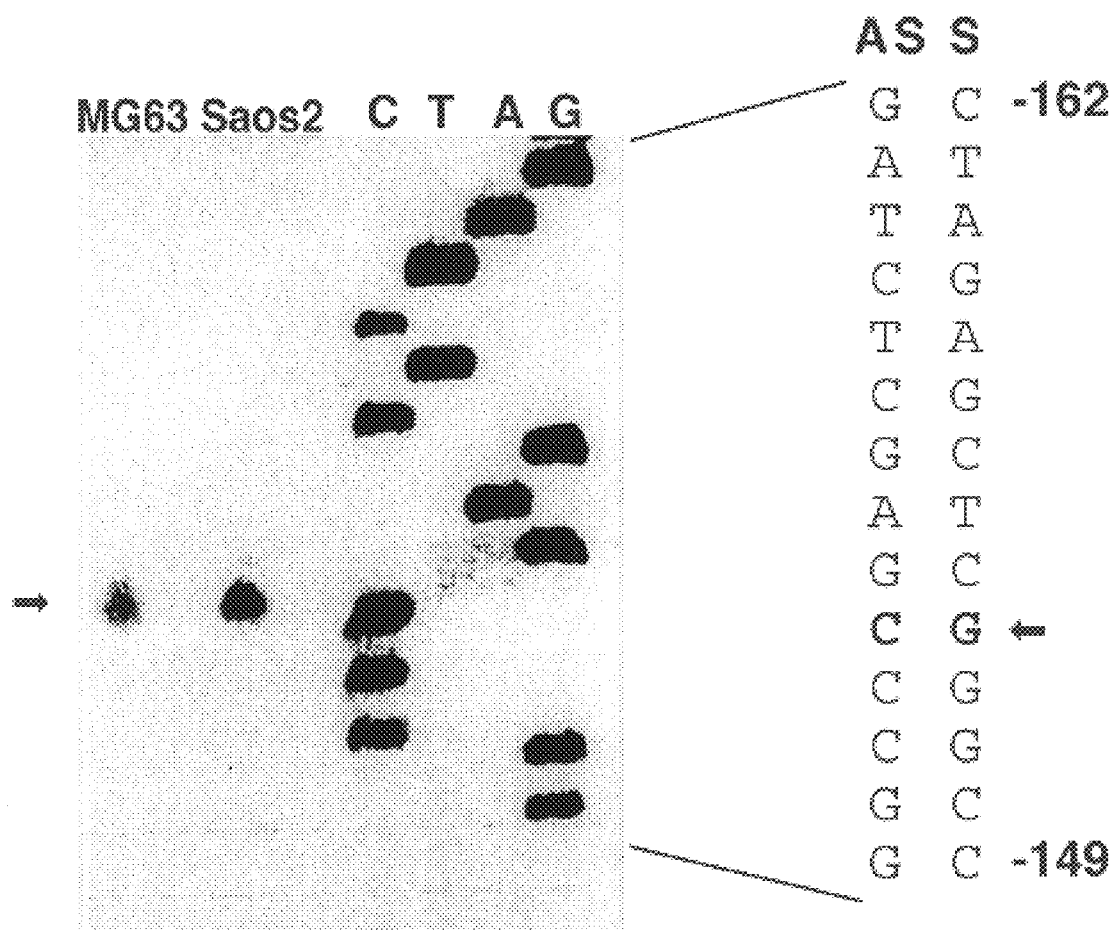
FIG. 2 shows the primer extension map of the human $p27_{Kip1}$ gene. Primer extension was performed according to the method described in Examples. The extension products based on the primer 0–128 are indicated using total RNAs from the MG63 cells and the Saos2 cells as templates. In this figure the antisense sequence ladder is shown. The arrowhead indicates a C residue (a G residue in the sense strand) as the presumed transcriptional start site. S stands for sense strand (SEQ ID NO:6) and AS for antisense strand (SEQ ID NO:5).

The term "compound" used herein include natural ones as well as synthetic ones, which may have low molecular weight or high molecular weight and may be organic or inorganic.

The present invention relates to a promoter of the human gene. More specifically, the present invention relates to a DNA existing in upstream of the human $p27_{Kip1}$ gene and having the promoter activity. The promoter DNA of the present invention comprises at least part of the nucleotide sequence of the 5' flanking region of the human $p27_{Kip1}$ gene. It may contain any nucleotide sequence of the 5' flanking region of the human p27$^{Kip1}$ gene as long as it retains the promoter activity. For example, such a DNA, existing in upstream of the human p27$_{Kip1}$ gene and having the promoter activity, includes the DNA having the nucleotide sequence of the 5' upstream positions −3568 to −12 of the human p27$_{Kip1}$ gene (corresponding to positions 1 to 3557 of SEQ ID NO:1, which shows the 5' upstream positions −3568 to −1 of the human p27$_{Kip1}$ gene), the DNA having the nucleotide sequence of the positions −1797 to −12 (corresponding to positions 1772 to 3557 of SEQ ID NO:1), and the DNA having the nucleotide sequence of the positions −774 to −12 (corresponding to positions 2795 to 3557 of SEQ ID NO:1).

On the other hand, the DNA having the nucleotide sequence of the 5' upstream positions −435 to −12 of the human p27$_{Kip1}$ gene (corresponding to positions 3134–3557 of SEQ ID NO:1) practically does not have the promoter activity. Considering the fact that the DNA having the nucleotide sequence of the positions −774 to −12 does have the promoter activity, it can be inferred that the nucleotide sequence between the 5' upstream positions −774 and −436 of the human p27$_{Kip1}$ gene (corresponding to positions 2795–3133 of SEQ ID NO:1) contains an essential region for the promoter activity. Therefore, the promoter DNA of the present invention preferably contains at least part of the nucleotide sequence between the 5' upstream positions −774 and −436 of the human p27$_{Kip1}$ gene. The upstream region of the human p27$_{Kip1}$ gene can be isolated by screening a human genomic library, using, for example, the nucleotide sequence of the human p27$_{Kip1}$ gene (Polyak, K., Lee, M.-H., Erdjument-Breomage, H., Koff, A., Roberts, J. M., Tempst, P., and Massague, J. (1994) Cell 78: 59–66; Toyoshima, H. and Hunter, T. (1994) Cell 78: 67–74) or part of it, or the nucleotide sequence described in SEQ ID NO:1 or part of it. The DNA according to the present invention can be synthesized based on the nucleotide sequence of SEQ ID NO:1 using the methods known in the art.

A person skilled in the art would readily prepare a DNA having the promoter activity equivalent to the activity of the wild type human p27$_{Kip1}$ gene promoter DNA, by modifying parts of the nucleotide sequence of the wild type promoter DNA through nucleotide substitutions, deletions, and additions. Thus, the promoter DNA of the present invention also includes the DNA having nucleotide sequence modified from the wild type sequence by nucleotide substitutions, deletions, and additions, which shows the promoter activity equivalent to that of the wild type promoter DNA. The nucleotide modifications can be done, for example, by deletion using restriction enzymes or exonucleases, mutation using the site-directed mutagenesis, modification of the promoter sequence using PCR with mutant primers, and direct introduction of synthetic mutant DNA.

The promoter DNA of the present invention can be used, for example, for the treatment or prevention of disorders related to the p27$_{Kip1}$ protein deficiency or abnormal expression thereof, both of which may result from the in vivo mutations of the promoter. Namely, by inserting the human p27$_{Kip1}$ gene containing the promoter DNA of the present invention (for example, the DNA having the nucleotide sequence described in SEQ ID NO:1) can be inserted into a vector such as retrovirus vectors derived from, for example, Molony murine leukemia virus (MoMuLV) or human immunodeficiency virus (HIV), adenovirus vectors, or adeno-associated virus vectors, or can be incorporated in liposome and the like, introduced into the somatic cells, to express the p27$_{Kip1}$ protein under the normal control, thereby ameliorating disorders related to the p27$_{Kip1}$ protein deficiency or abnormal expression thereof.

If it becomes clear that the promoter DNA of the present invention is activated by a particular stimulus, it would be possible to express a desired gene inducibly, by preparing a vector or the like into which the DNA of present invention is inserted upstream of the desired gene, introducing it into the somatic cells, and applying the stimulus. For example, if a cytocidal gene is used as the desired gene, it would be possible, to selectively destroy the cells, into which the promoter DNA of the present invention has been introduced, by applying the stimulus. Such use of the promoter DNA of the present invention is applicable to a broad range of diseases, such as cancers, in which there are cells to be destroyed.

The present invention also relates to a DNA containing at least part of the sequence of the promoter DNA of the present invention described above (including its derivatives). Such a DNA can competitively inhibit the binding between the promoter DNA of the present invention and proteins (for example, transcription factors) that can bind to it, regardless of whether or not it has the promoter activity. Consequently, if the DNA is the binding site for a protein that inhibits the promoter activity of the promoter DNA of the present invention, the promoter activity can be enhanced in this way. On the other hand, if it is the binding site for a protein that enhances the promoter activity of the promoter DNA of the present invention, the promoter activity can be inhibited in this way.

The DNA to be used for the competitive inhibition usually has a length of at least 6 bases or more, and more preferably 10 bases or more. Examples of the DNA to be used for the competitive inhibition include sequences containing the consensus binding sites for the transcription factors described in FIG. 1 and FIG. 5. Since the p27 protein is known to stop the cellular proliferation, it would be effective to enhance the activity of the promoter DNA of the present invention for the treatment of proliferative cellular diseases, such as malignant tumors, arteriosclerosis, and restenosis caused by the endothelial proliferation after the balloon coronary angioplasty. On the other hand, the inhibition of the activity of the promoter DNA of the present invention would be effective for the treatment of diseases that require cellular proliferation, such as aplastic anemia, cirrhosis, or wound healing.

As the vector comprising the promoter DNA of the present invention, any vector can be used as long as the DNA can function therein. For use in gene therapy, the vectors as described above can be used. For use in an assay or an experiment, commercially available vectors such as pGL3 (Promega) or Retro-X™ System (CLONTECH) can be used.

As the cell carrying the above vector, any cell can be used as long as the vector can be transfected thereinto and can function therein. For example, the mammalian cell lines, preferably human-derived cell lines can be used, such as U2OS with intact p53 and RB genes, Saos2 and C33A with both mutated p53 and RB genes, or MG63 cells with mutated p53 gene.

For regulating the activity of the promoter DNA of the present invention, it is possible to apply the method in which a protein capable of regulating the activity of the promoter DNA of the present invention is used, in addition to the competitive inhibition using partial sequences of the promoter DNA of the present invention as described above. The promoter DNA of the present invention can be utilized to screen a protein that regulates the promoter activity. Therefore, the present invention also relates to a method of screening a protein capable of regulating the activity of the promoter DNA of the present invention. The proteins which regulate the activity of the promoter DNA of the present invention include the proteins that indirectly enhance or inhibit the activity of the promoter DNA of the present invention by acting on membrane receptors or intracellular proteins as well as the proteins which enhance or inhibit its activity by directly binding to the promoter DNA of the present invention.

One embodiment of the screening method of the present invention includes the steps of bringing a test protein sample into contact with the DNA of the present invention and selecting a protein that binds to the DNA of the present invention. Such a method can be carried out by, for example, affinity purification of the proteins binding to the DNA using the promoter DNA of the present invention. A specific example of the method comprises the steps of labeling the promoter DNA of the present invention with biotin, binding it to magnetic beads conjugated with streptavidin to make the DNA affinity beads, incubating the beads with the nuclear extract of the cell to purify the proteins in the extract that specifically bind to the promoter DNA of the present invention, and determining their structures. By this method, it is possible to purify proteins that directly bind to the promoter DNA of the present invention and proteins that do not directly bind to the promoter DNA of the present invention but bind to, it by forming a complex with the proteins directly binding to the promoter DNA as subunits thereof (Gabrielsen, O. S. et al., (1989) Nucleic Acid Research 17: 6253–6267; Savoysky, E. et al., (1994) Oncogene 9: 1839–1846).

Another embodiment includes the steps of introducing a test DNA into cells carrying a reporter gene fused downstream of the DNA of the present invention and selecting an expression product that regulates the reporter gene expression. This method includes, for example, the one-hybrid method using yeast or animal cells. Specifically, the method can be carried out by stably transfecting into cells a reporter gene in which the promoter DNA of the present invention has been inserted, transfecting a gene library into the cells, selecting clones that enhance or inhibit the reporter gene expression to determine proteins that bind to the promoter DNA of the present invention. By this method, it is possible to obtain, in addition to the proteins that directly bind to the promoter DNA of the present invention, the proteins that indirectly regulate the activity of the promoter DNA of the present invention by acting on cellular endogenous protein. Regarding such methods as the yeast one-hybrid method(Li, J. J. and Herskowitz, I. (1993) Science 262:1870–1873 Wang, M. M. and Reed, R. R. (1993) Nature 364:121–126), MATCHMAKERS SYSTEM (CONETECH) and other kits are already commercially available.

For example, the reporter gene used in the screening method as described above and below includes, luciferase, chloramphenicol acetyltransferase (CAT), and the like. For the cell-based assay, the following commercially available reporter plasmids can be used, such as pGL2, pGL3, or pRL (Promega) with luciferase gene, or pCAT3 (Promega) with CAT gene. The cells that can be in the screening method include those as described above.

Still another embodiment includes the steps of bringing a test sample into contact with cells carrying a reporter gene fused downstream of the promoter DNA of the present invention and selecting a protein that regulates the reporter gene expression. A specific example of the method comprises incubating cells stably transfected with a reporter gene into which the promoter DNA of the present invention has been inserted and test samples (such as culture supernatant of the cells transfected with a gene library), and selecting proteins that enhance or inhibit the reporter gene expression. This method enables screening of proteins that indirectly influence the activity of the promoter DNA of the present invention through receptors on the cell membrane and the like.

Using the DNA of the present invention, it is also possible to directly isolate a DNA encoding a protein that regulates the promoter activity of the DNA of the present invention. The present invention thus also relates to a method of screening a DNA encoding a protein that regulates the promoter activity of the DNA of the present invention. One embodiment of this screening method comprises the steps of bringing an expression product of a test DNA-into contact with the DNA of the present invention and selecting the DNA encoding the expression product that binds to the DNA of the present invention. The method includes, for example, the southwestern technique. Specifically, the method is carried out by causing expression of each protein in the E. coli cells in a gene library has been introduced, transferring the protein onto a filter membrane, directly blotting it using the promoter DNA of the present invention as a probe, selecting the clone expressing the protein that binds to the DNA probe, and isolating the gene encoding the protein. By this method, it is possible to obtain the gene encoding the protein that has activity to bind to the DNA of the present invention.

Another embodiment comprises the steps of introducing a test DNA into cells carrying a reporter gene fused downstream of the DNA of the present invention and selecting the DNA encoding the expression product which regulates the reporter gene expression. This method includes, for example, the above-described one-hybrid method using yeast or animal cells. Namely, the method can be carried out by stably transfecting into cells a reporter gene in which the promoter DNA of the present invention has been inserted, transfecting the cells with a gene library, selecting a clone that enhance or inhibit the reporter gene expression, and screening the gene encoding the protein which binds to the promoter DNA of the present invention. By this method, it is possible to obtain, in addition to the gene encoding the protein that directly binds to the promoter DNA of the present invention, the gene encoding the protein which indirectly regulates the activity of the promoter DNA of the present invention by acting on cellular endogenous protein.

Still another embodiment comprises the steps of bringing an expression product of a test DNA into contact with cells carrying a reporter gene fused downstream of the DNA of the present invention and selecting a DNA encoding an expression product that regulates the reporter gene expression. A specific example of the method can be carried out by incubating cells stably transfected with a reporter gene into which the promoter DNA of the present invention has been inserted and a test sample (such as culture supernatant of cells transfected with a gene library), isolating the protein that enhances or inhibits the reporter gene expression or the gene encoding it. By this method, it is possible to obtain the gene encoding the protein that indirectly influences the activity of the promoter DNA of the present invention through receptors on the cell membrane and the like.

By using the promoter DNA of the present invention, it is also possible to screen synthetic compounds that regulate the activity as well as the protein that regulates the activity of the promoter DNA or the gene encoding it. Thus, the present invention also relates to a method of screening a synthetic compound that regulates the promoter activity of the promoter DNA of the present invention. One embodiment of the screening method comprises the steps of bringing a test sample into contact with the promoter DNA of the present invention in the presence of a test compound and selecting a compound which promotes or inhibits the binding between the promoter DNA of the present invention and a protein in the test sample. For example, the method can be carried out by binding a cell nuclear extract to the promoter DNA of the present invention which has been labeled with an isotope and the like, subjecting the binding product to polyacrylamide gel electrophoresis, and detecting, by gel shift assay, the band representing the complex between the protein in the nuclear extract and the promoter DNA of the present invention. When adding the DNA probe, the test compound is also added to select a compound that enhances or inhibits the formation of the bands representing the complex between the protein in the nuclear extract and the promoter DNA of the present invention. This method enables screening of compounds that directly act on the promoter DNA of the present invention and compounds that act on the proteins binding to the promoter DNA of the present invention. If, for example, a protein that binds to the promoter DNA of the present invention inhibits the activity of the promoter DNA of the present invention in vivo, compounds that inhibit the binding between the protein and the promoter DNA of the present invention would enhance the activity of the promoter DNA of the present invention. Furthermore, if the protein that binds to the promoter DNA of the present invention has already been isolated, then it is also possible to use a recombinant protein of the protein in place of the cell nuclear extract.

Another embodiment comprises the steps of bringing a test compound into contact with cells carrying a reporter gene fused downstream of the promoter DNA of the present invention and selecting a compound that regulates the reporter gene expression. For example, the method can be carried out by transfecting cells with a luciferase gene vector into which the promoter DNA of the present invention has been inserted upstream to prepare the cells capable of stably expressing the luciferase activity under the control of the promoter DNA of the present invention, incubating the cells with a test compound in the culture medium, measuring the activity of the promoter DNA of the present invention with the luciferase activity as an indicator, and selecting a compound that enhances or inhibits the promoter activity. Compounds that directly or indirectly regulate the activity of the promoter DNA of the present invention can be obtained by this method.

If the protein that regulates the activity of the promoter DNA of the present invention has already been obtained, it is possible to screen compounds that regulate the activity of the promoter DNA of the present invention by bringing the protein (or its derivative) into contact with the promoter DNA of the present invention in the presence of test compounds and selecting the compounds that enhance or inhibit the binding between the protein (or its derivative) and the promoter DNA of the present invention. Specifically, this method can be carried out by, for example, purifying the protein (or the DNA binding domain thereof alone) that binds to the promoter DNA of the present invention, which is fused with glutathion S-transferase, binding it to the microplate coated with the anti-glutathion S-transferase antibody, bringing the biotin labeled promoter DNA of the present invention into contact with the above protein, and detecting the binding between the protein and the promoter DNA of the present invention using alkaline phosphatase coupled to streptavidin. When adding the promoter DNA of the present invention, a test compound is also added to select the compound that enhances or inhibits the binding between the protein and the promoter DNA of the present invention. By this method, it is possible to obtain compounds that directly act on the promoter DNA of the present invention and compounds that act on the proteins that bind to the promoter DNA of the present invention. If, for example, the protein binding to the promoter DNA of the present invention inhibits the activity of the promoter DNA of the present invention in vivo, compounds that inhibit the binding between the protein and the promoter DNA of the present invention would enhance the activity of the promoter DNA of the present invention.

Furthermore, if the activity of the promoter DNA of the present invention is controlled through its own modification by DNA methylation enzymes and the like, the promoter DNA of the present invention can be used to screen compounds that enhance or inhibit the enzyme activity. In the case of using DNA methylation enzymes, when intake of methyl groups into the promoter DNA of the present invention is measured using an isotope, test compounds are added in advance to selectively screen compounds that enhance or inhibit intake of methyl groups.

If the compounds isolated by means of the above screening method are low molecular weight compounds, such compounds are advantageously used in gene therapy because they do not suffer from problems of the poor introduction efficiency of the gene or the safety of vectors. In the case that the proteins themselves are deficient or inactivated, like p53, Rb, and p16 in malignant tumors, it is necessary to introduce the normal genes in order to supplement their activities and it would be of no merit to activate the promoter. In this respect, in the case of malignant tumors or the like, $p27^{Kip1}$ seldom loses its activity by mutation itself, but rather, only its expression is reduced. Therefore, in most cases, activation of the promoter DNA of the present invention caused by administering the compound that enhances the promoter activity would result in the expression of the normal $p27_{Kip1}$ protein in cells, thereby stopping proliferation of cells through the inhibition of cyclin/cdk. Thus, based on this system, it would be possible to effectively treat malignant tumors.

The present invention provides the human $p27^{Kip1}$ gene promoter. It enables the gene therapy utilizing the promoter and the screening of proteins and drugs that regulate the activity of the promoter, thereby controlling the expression of the p27 protein.

The following Examples will illustrate the present invention in more detail, but are not construed to limit the scope of the invention.

EXAMPLE 1

Cell Culture

Human osteosarcoma cell lines Saos2 and U2OS, and human cervix cancer cell line C33A (purchased from the American Type Culture Collection, Manassas, Va., USA) were maintained in Dulbecco's modified Eagle medium containing 10% fetal calf serum, and incubated at 37° C. in a humidified atmosphere of 5% $CO_2$. In U2OS cells, the p53 and RB genes are intact (Huang, H.-J. S., Yee, J.-K., Shew, J.-Y., Chen, P.-L., Bookstein, R., Friedmann, T., Lee, E. Y.-H. P., and Lee, W.-H. (1988) Science 242: 1563–1566), while both the p53 and RB genes are mutated in Saos2 cells (Huang, H.-J. S., Yee, J.-K., Shew, J.-Y., Chen, P.-L., Bookstein, R., Friedmann, T., Lee, E. Y.-H. P., and Lee, W.-H. (1988) Science 242: 1563–1566; Chen, P.-L., Chen, Y., Bookstein, R., and Lee, W.-H. (1990) Science 250: 1576–1580) and in C33A cells (Scheffner, M., Munger, K., Byrne, J. C. and Howley, P. M. (1991) Proc. Natl. Acad. Sci. USA 88: 5523–5527).

EXAMPLE 2

Cloning of Human p27$^{Kip1}$ Promoter Fragment

The human p27$^{Kip1}$ cDNA in the plasmid BLUESCRIPT SK-p27$^{Kip1}$ (obtained from Dr. J. Massague of the Memorial Sloan-Kettering Cancer Center, USA) was digested with EcoRI and PstI to obtain a part of the human p27$^{Kip1}$ cDNA containing exon 1, which was used as a probe to screen a human leukocyte genomic library. Using this probe, approximately $10^6$ phage plaques of a human leukocyte genomic library constructed in the EMBL3 SP6/T7 phage vector (Clontech, Palo Alto, Calif., USA) were screened to obtain the genomic DNA fragments containing the 5' region of the human p27$^{Kip1}$ gene. Hybridization was performed in a buffer containing 5×SSC, 50% formaldehyde, 1% SDS, 5×Denhardt's solution, and 0.1 µg/µl of denatured sonicated fish sperm DNA at 42° C. for over 16 hours. One positive phage plaque was amplified, and its DNA was purified. The genomic DNA fragments were digested with several restriction enzymes and analyzed by Southern blotting.

EXAMPE 3

Sequence Analysis of Human p27$^{Kip1}$ Promoter

The approximately 4.8 kb XhoI fragment derived from the positive phage DNA was subcloned into the plasmid BLUESCRIPT SK+(Stratagene, La Jolla, Calif., USA) and its sequence was determined. This fragment contained a 5' proximal region, the first exon, and the first intron. The sequence of the 5' untranslated region of the genomic DNA fragment was identical to that of the human p27Kip1 cDNA probe. A computer search for candidates of the regulatory factors within the promoter region using the GENETYX software (Software Development Co., Tokyo, Japan) revealed the presence of binding sites for multiple transcription factors such as Sp1, PEA3, CTF, Myb, PEBP2, AP2, NF-κB, and ATF, which control the p27$^{Kip1}$ gene expression at the transcriptional level (FIG. 1). As a result of analysis of the region surrounding the transcriptional start site, no existence of the TATA box was observed.

EXAMPLE 4

Transcriptional start Site for Human p27Kip1 Promoter

In order to determine the transcriptional start site, two 20-bp oligonucleotide, O-128 (5'-CCCAGCGACTGCCCTCGGAG-3', SEQ ID NO:2) which is complementary to the nucleotide positions −120 to −101, and O-234 (5'-CCCTCTCGGAAGCCCAGCGA-3', SEQ ID NO: 3) which is complementary to the nucleotide positions −108 to −89, were end-labeled using [γ-32P]ATP and T4 polynucleotide kinase (Toyobo, Osaka, Japan). These extension primers were hybridized with 20 µg of the total RNA isolated from the human osteosarcoma cell lines MG63 and Saos2 at 42° C., The annealed primers were extended with 200 units of the enzyme SUPERSCRIPT II transcriptase (Gibco BRL, Gaithersburg, Md., USA) at 42° C. for 50 minutes. The products thus obtained were analyzed on a 6% polyacrylamide non-denaturing gel in parallel with a sequencing reaction generated with the same extension primers. The two primers were reproducibly extended up to the identical G residue at the position −153 upstream of the translation start site, using the mRNks derived from these two cell lines (FIG. 2). The position was presumed to correspond to the major transcriptional start site. There are also possibilities that two additional transcriptional start sites may exist at upstream positions −225 and −247.

EXAMPLE 5

Promoter Activity and Deletion Analyses of Human p27$^{Kip1}$ Promoter

Figure 3:
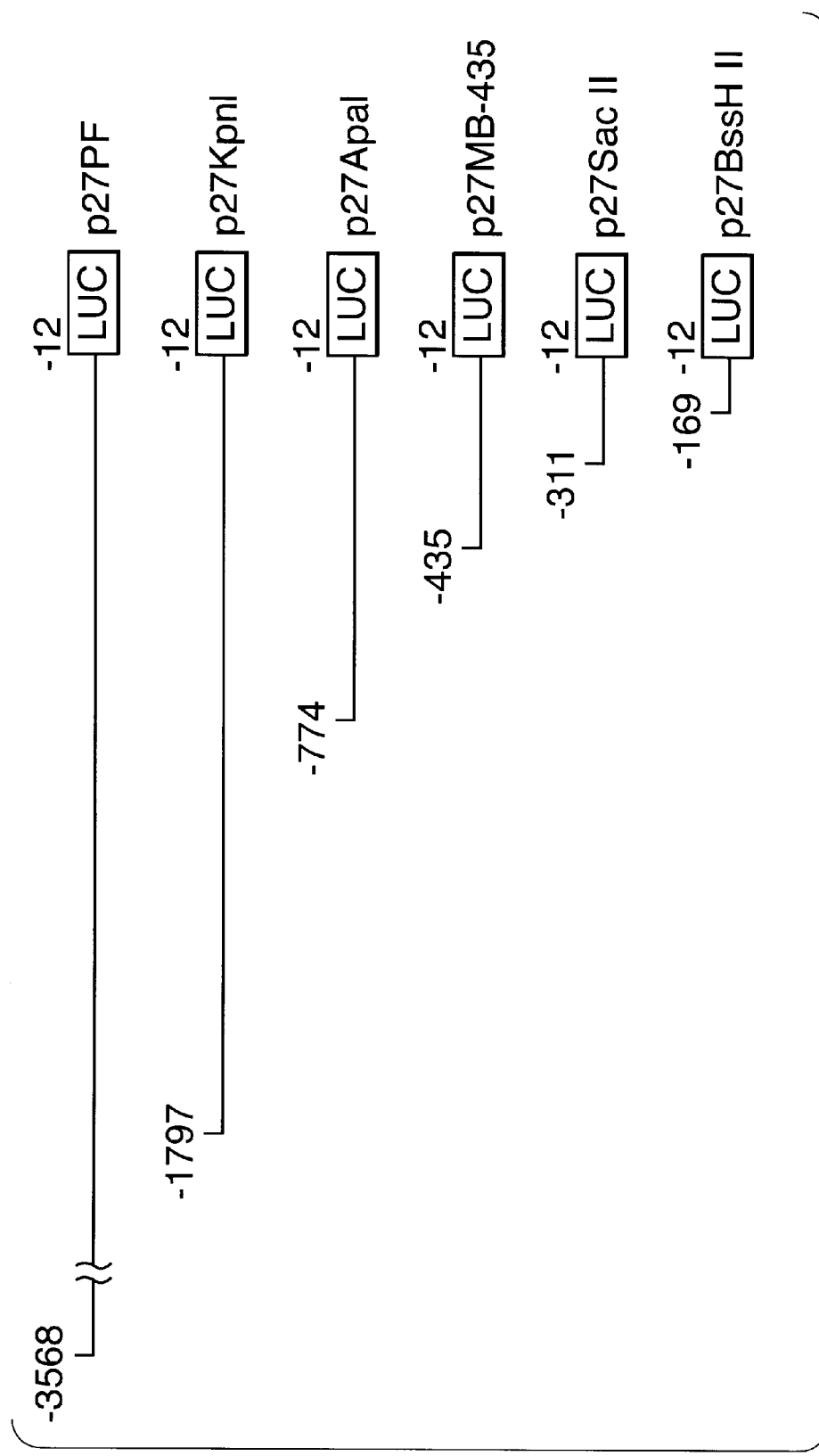
FIG. 3 shows the deletion mutants of the human $p27_{Kip1}$ promoter-luciferase constructs. The full length human $p27_{Kip1}$ promoter-luciferase construct, p27PF, was prepared by subcloning a DNA fragment, which spans from the XhoI site (position −3568) to the SmaI site (position −12) in front of the luciferase reporter gene in pGVB2. The 5' deletion constructs were made by utilizing restriction enzyme sites or the Mungbeans Exonuclease III system.

An approximately 3.5 kb fragment spanning from −3568 to −12 upstream of the translation start site of the human p27$^{Kip1}$ gene was subcloned into the luciferase reporter plasmid pGVB2 (Nippon Gene, Tokyo,. Japan); This human p27$^{Kip1}$-luciferase fusion plasmid was named "p27PF". In order to generate deletion mutants of "p27PF", "p27PF" was treated separately with KpnI, ApaI, SacII, and BssHII. These restriction sites were blunt-ended with Klenow fragment or T4 DNA polymerase, and then self-ligated. These plasmids were designated "p27KpnI", "p27ApaI", "p27SacIII", and "p27BssHII", respectively. Another deletion mutant, designated "p27MB-4351", was generated by using the Mungbeans-Exonuclease III system, the "Kilo-sequence Deletion Kit" (Takara, Tokyo, Japan). All the generated constructs (FIG. 3) were confirmed by sequencing. The sequence was determined by the dideoxynucleotide chain termination method using "USB sequenase version 2.0 DNA sequence kit" (Amersham, Buckinghamshire, England). The primers used for the sequence determination were T3, T7, and synthetic oligonucleotides derived from the genomic DNA sequence.

Figure 4A:
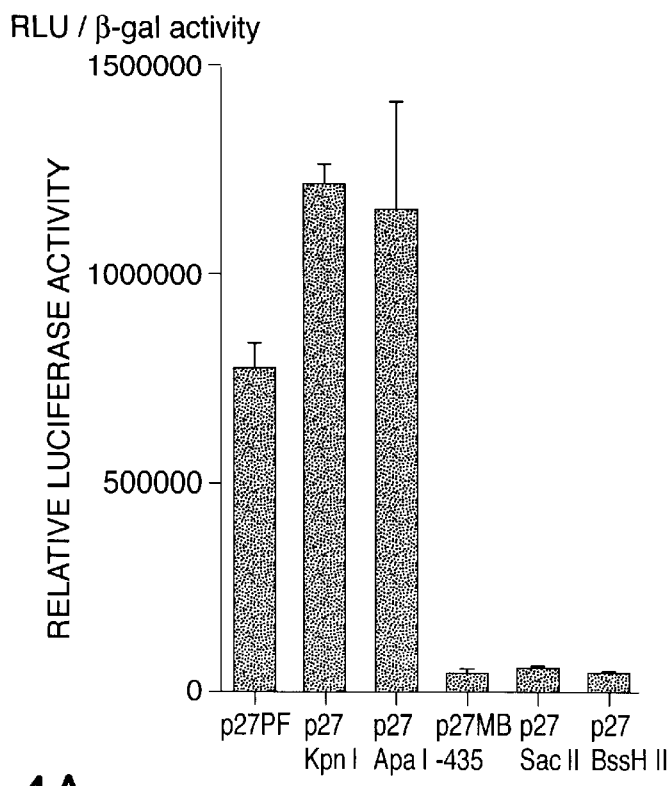
FIG. 4 shows the basal promoter activities of the human $p27_{Kip1}$ promoter constructs. Transcription was performed, according to the method described in Examples, using the C33A cells (a) and the Saos2 cells (b) with the various 5' deleted human $p27_{Kip1}$ promoter-luciferase constructs. The luciferase activity was standardized by the β-galactosidase activity produced by the co-transfected RSV-β gal plasmid.
Figure 4B:
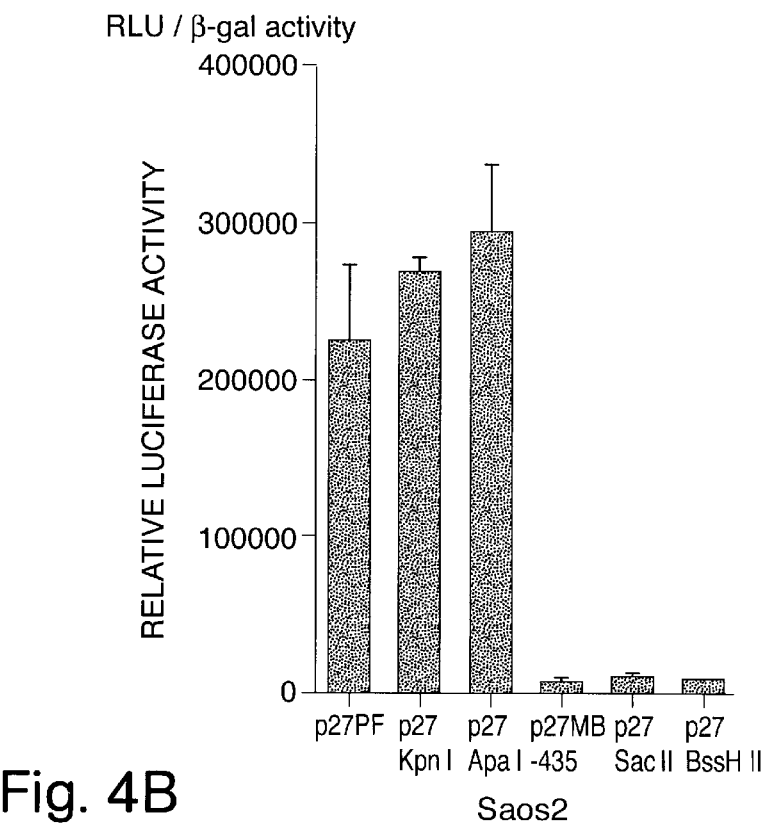

Subsequently, C33A cells and Saos2 cells were transiently transfected with the series of 5' deletion constructs. Specifically, C33A cells ($5 \times 10^5$ cells) and U2OS cells ($3 \times 10^5$ cells) were seeded in 6 cm-diameter tissue culture dishes, and 24 hours later, 2 µg of the plasmid and 1 µg of RSV β-gal, which contains the β-galactosidase gene under the control of the Rous sarcoma virus promoter (for normalizing the transfection efficiency), were co-transfected into the cells using the calcium phosphate co-precipitation method (Sambrook, J., Fritsch, E. F. and Maniatis, T. (1989) Molecular cloning: A laboratory manual, 2nd Ed., Cold Spring Harbor Laboratory, Cold Spring Harbor, N.Y.). The luciferase activity measurement 48 hours later did not show any significant difference in promoter activities between the human p27$^{Kip1}$ full-length promoter construct "p27PF" and the deletion constructs "p27KpnI" and "p27ApaI". However, in C33A cells and Saos2 cells (FIGS. 4a and 4b) and in U20S cells (data not shown), the promoter activity of the p27MB-435 construct was notably decreased by about 15- to 20-fold compared with that of the p27ApaI construct. This decrease in promoter activity indicates that the essential transcription factor binding sites or enhancer sites for the p27$^{Kip1}$ promoter activity could exist within this region. The luciferase activities of the cell lysates were measured according to the method described in "Brasier, A. R., Tate, J. E. and Habener, J. F. (1989) Biotechniques 7: 1116–1122" and standardized by the µ-galactosidase activities in the celllysates. All the transfection assays were done 3 times each. Each experiment was repeated at least twice.

EXAMPLE 6

Comparison Between Human and Murine p27$^{Kip1}$ Promoter Sequences The comparison of the human and murine p27$^{Kip1}$ promoter sequences by a computer analysis using GENETYX software revealed that the human p27$^{Kip1}$ promoter sequence is highly homologous to the murine p27$^{Kip1}$ promoter sequence (FIG. 5) (Kwon, T. K., Nagel, J. E., Buchholz, M. A., and Nordin, A. A. (1996) Gene 180: 113–120). The human sequence of the region from nucleotide position –774 to position –435 (FIGS. 4a and 4b), which contains the region necessary for the basal promoter activity, had 85% homology to the murine sequence. This suggests that necessary consensus transcription factors may act on this region. The putative transcription factor binding sites in this region are three consensus Sp1 sites, an AP2 site, two CTF sites, and an ATF site (FIG. 5). Among these, the two CTF and ATF sites are conserved, but other unknown conserved sites might be important for the basal p27$_{Kip1}$ promoter activity.

What is claimed is:

1. A method of screening for a protein that regulates promoter activity of a human p27$^{Kip1}$ promoter DNA, said promoter DNA containing at least a substantial part of a region extending from position 2795 to 3133 of SEQ ID NO:1, wherein said promoter DNA retains the ability to promote the expression of a human p27$^{Kip1}$ gene, said method comprising a step selected from the group consisting of:

(a) bringing a test sample, said sample containing a test protein, into contact with said promoter DNA and selecting the protein that binds to said promoter DNA;

(b) introducing a test DNA coding for a test protein into cells carrying a reporter gene coding for an expression product fused downstream of said promoter DNA, testing for the presence of said reporter gene expression product, and selecting the test protein that regulates reporter gene expression; and (c) bringing a test sample, said sample containing a test protein, into contact with cells carrying a reporter gene coding for an expression product fused downstream of said promoter DNA, testing for the presence of said reporter gene expression product, and selecting the test protein that regulates reporter gene expression.

* * * * *

UNITED STATES PATENT AND TRADEMARK OFFICE
CERTIFICATE OF CORRECTION

PATENT NO.    : 6,524,796 B1
DATED         : February 25, 2002
INVENTOR(S)   : Toshiyuki Sakai et al.

It is certified that error appears in the above-identified patent and that said Letters Patent is hereby corrected as shown below:

Title page, Item [54] and Column 1, line 1,
Replace "$P27^{KIP1}$" with -- $p27^{Kip1}$ --;

Column 7,
Line 53, replace "MATCHMAKERS SYSTEM" with -- MATCHMAKER SYSTEMS --;

Column 15,
SEQ ID NO 2, after "<213> ORGANISM:"; replace "Homo sapiens" with -- Artifical Sequence --;

Column 17,
SEQ ID NO 3, after "<213> ORGANISM:"; replace "Homo sapiens" with -- Artifical Sequence --;
SEQ ID NO 5, after "<213> ORGANISM:"; replace "Homo sapiens" with -- Artifical Sequence --;
SEQ ID NO 6, after "<213> ORGANISM:"; replace "Homo sapiens" with -- Artifical Sequence --;

Column 21,
Line 13, replace "SEQ I)" with -- SEQ ID --.

Signed and Sealed this

Fifth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,524,796 B1                                                Page 1 of 1
DATED        : February 25, 2003
INVENTOR(S)  : Toshiyuki Sakai et al.

It is certified that error appears in the above-identified patent and that said Letters Patent is hereby corrected as shown below:

Column 7,
Line 53, replace "(CONETECH)" with -- (CLONTECH) --

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO. : 6,524,796 B1  Page 1 of 1
DATED : February 25, 2003
INVENTOR(S) : Toshiyuki Sakai et al.

It is certified that error appears in the above-identified patent and that said Letters Patent is hereby corrected as shown below:

<u>Title page, Item [54] and Column 1, line 1,</u>
Replace "P27<sup>KIP1</sup>" with -- p27$^{Kip1}$ --;

<u>Column 7,</u>
Line 53, replace "MATCHMAKERS SYSTEM" with -- MATCHMAKER SYSTEM --;

<u>Column 15,</u>
SEQ ID NO 2, after "<213> ORGANISM:"; replace "Homo sapiens" with -- Artifical Sequence --;

<u>Column 17,</u>
SEQ ID NO 3, after "<213> ORGANISM:"; replace "Homo sapiens" with -- Artifical Sequence --;
SEQ ID NO 5, after "<213> ORGANISM:"; replace "Homo sapiens" with -- Artifical Sequence --;
SEQ ID NO 6, after "<213> ORGANISM:"; replace "Homo sapiens" with -- Artifical Sequence --;

<u>Column 21,</u>
Line 13, replace "SEQ I)" with -- SEQ ID --.

This certificate supersedes Certificate of Correction issued August 5, 2003.

Signed and Sealed this

Fourth Day of May, 2004

JON W. DUDAS
*Acting Director of the United States Patent and Trademark Office*

SEQUENCE LISTING

<160> NUMBER OF SEQ ID NOS: 8

<210> SEQ ID NO 1
<211> LENGTH: 3568
<212> TYPE: DNA
<213> ORGANISM: Homo sapiens

<400> SEQUENCE: 1

```
ctcgaggaag gactgaaact gtgtgcttgc ggtgggaggg gcagctgggc aaggaaccgt      60
gaaccttcgc agaaacattt ggggctgcag aacttgggtg agagcgctgc atctgggagc     120
tggcgacgct ggcggcttgc tcattcaccc catctgaaca cttgtctatg acacaggtgt     180
tttctcttaa gttattttgg tctttgcctc tctcctcagg ttgtgaagat tacagaaatc     240
tgggatggct tatgggacgc ttctcagccc taagtaggaa aacagcagtg aaaatggcaa     300
ccaaaacatc acgcaggact gggggttttg gggaaacagc tcactttaga gcagtgcagt     360
gtagagcttt ccgtcttcta ccagggtcca cctttaacac tgtttatctg aaaattttcc     420
ccctggctta ctcgcttgca gctgcccact ttgcagaagg atggcgctct gatctctacg     480
ctccctgttc cttcagggac tccatagtat tttttttcac gcgtcgtcgc tactacagca     540
gacgcctgcg ttctcattat ttgctgtaca gatctccggt gccttgactg taaacaaaac     600
actttagatc attgtgaggt cgatgtaagc acagcctttc tgctggcagc cagacttctt     660
aaggtggtgt gactgtgact tgcttacttt tcgagatcaa caacaacaaa gcgacaaaat     720
ggtgctccta catattagtt gaaagattca gcatgtgaag gggatcgaag tgtttatttt     780
ccacttccat ataagacatg aattccatga gtaaaatcaa cttctgtggc aaggtgaact     840
actctagaat gtctccattt acatacatgt ggtagtttgg atgtttatgc atatggatag     900
atgcacatat atagagttcc tgtgttgtct agcaattgtt ttaaaatttg gacaattatc     960
taatttctag ggtaaggtat aaattatggt agggaggcct accctaattt tcctgttcct    1020
tttcccccag tctgcagtcc aataaattga cagccttaaa agtagaaaaa ctaaagagga    1080
tgagacctct tgcttgatcc taggtgaatt cttttctgtc agttaggtag gaagtcctga    1140
cttgaaaact agttctgggc actgccccct ttactgttct ctgggtatca accctgtcc    1200 ttcaatttta gttgaactag tggatggtga taccacaggc tcaagacagc tgcatttaaa    1260
tatcagtgac cacaggccac atcaaggaaa catctgcagg caacccaggg cctgggaagg    1320
agccatttca gtcacttgta agacagcagg acctgcagac tacagcacaa tcaaactcag    1380
acaaaaccct gaaccagtga gaaccattag gaaggaaagg aacagaaaat gaaccaacct    1440
gagtgttagg agacttgcat ctagtcctga ctccggtacc aaccgaatgc atgtccctgg    1500
acaggaaacc tctctgagtc tcgatttcct ccgtggtaaa aaggagaggg ttaaaccaca    1560
gggtcccgag ggtcccttcc agctgtcaca ttctggagcg tatgagatga ggtaggcaca    1620
caaagtggac aagatgtggc taagaaaaca agctacacat caagctcatc tgtagcatag    1680
```

-continued

```
gtgcttaaga aaactttgct gctgtgtaat attagaacgg aaggttggtt tccagtaaaa    1740
tgcattaact ttggctcaaa ccaagatgat gggtaccggg catgggggtg gggaggcagt    1800
tgaagatcca ctgagctttg tctcagggca gccctgctca tcgtcctact ttaccttcca    1860
ccacggtgct caagcccaca ctgagagaga aatttccagc tgcaaaaggg agaagagaaa    1920
cgctggaata ctagtatcgg acgttaggac atggttgtgg tgttttaaaa atcatttcat    1980
catctggagt ttgaccccga ggggagtatt ttcacccttc agccctctga aagcattcac    2040
tagcatctga atattgttct gagtttgttg gagcagtgaa atctggtgag agagaagggt    2100
ggaggaagga aggagctgtt gtatttggcg gctggactca ggtagaggaa actgctacaa    2160
tcccgggaaa gaacagaaaa gtagaaaggg acgagttccc acacgcagcc aatgtccatg    2220
gccttaactg tgcttgggaa ggaagatcct gggccagggg tgtaccctcg ttttccaaaa    2280
actaaacgtg tctgagacag ctacaaagtt tattaaggga cttgagagac tagagttttt    2340
tgttttttt ttttaatctt gagttccttt cttattttca ttgagggaga gcttgagttc    2400
atgataagtg ccgcgtctac tcctggctaa tttctaaaag aaagacgttc gctttggctt    2460
cttccctagg ccccccagcct ccccagggat ggcagaaact tctgggttaa ggctgagcga    2520
accattgccc actgcctcca ccagccccca gcaaaggcac gccggcgggg gggcgcccag    2580
cccccccagc aaacgctccg cggcctcccc cgcagaccac gaggtggggg ccgctgggga    2640
gggccgagct gggggcagct cgccaccccg gctcctagcg agctgccggc gaccttcgcg    2700
gtcctctggt ccaggtcccg gcttcccggg agaggagcgg gagggaggtc ggggcttagg    2760
cgccgctgcg aacccgccaa cgcagcgccg ggccccgaac ctcaggcccc gccccaggtt    2820
cccggccgtt tggctagttt gtttgtctta attttaattt ctccgaggcc agccagagca    2880
ggtttgttgg cagcagtacc cctccagcag tcacgcgacc agccaatctc ccggcggcgc    2940
tcggggaggc ggcgcgctcg ggaacgaggg gaggtggcgg aaccgcgccg gggccacctt    3000
aaggccgcgc tcgccagcct cggcggggcg gctcccgccg ccgcaaccaa tggatctcct    3060
cctctgttta aatagactcg ccgtgtcaat cattttcttc ttcgtcagcc tcccttccac    3120
cgccatattg ggccactaaa aaaggggggc tcgtcttttc ggggtgtttt tctcccctc     3180
ccctgtcccc gcttgctcac ggctctgcga ctccgacgcc ggcaaggttt ggagagcggc    3240
tgggttcgcg ggaccgcggg cttgcacccg cccagactcg gacgggcttt gccaccctct    3300
ccgcttgcct ggtcccctct cctctccgcc ctccgctcg ccagtccatt tgatcagcgg     3360
agactcggcg gccgggccgg ggcttccccg cagcccctgc gcgctcctag agctcgggcc    3420
gtggctcgtc ggggtctgtg tcttttggct ccgagggcag tcgctgggct tccgagaggg    3480
ggttcgggcc gcgtaggggc gctttgtttt gttcggtttt gttttttgta gagtgcgaga    3540
gaggcggtcg tgcagacccg ggagaaag                                      3568
```

<210> SEQ ID NO 2
<211> LENGTH: 20
<212> TYPE: DNA
<213> ORGANISM: Homo sapiens

<400> SEQUENCE: 2
cccagcgact gccctcggag                                               20

<210> SEQ ID NO 3
<211> LENGTH: 20
<212> TYPE: DNA
<213> ORGANISM: Homo sapiens

-continued

<400> SEQUENCE: 3
ccctctcgga agcccagcga                                                  20

<210> SEQ ID NO 4
<211> LENGTH: 814
<212> TYPE: DNA
<213> ORGANISM: Murine

<400> SEQUENCE: 4
cctagatccc cgggtccctg cctggccgcc gcgctggccc ctccccagct ctccggccgt      60
ttcgtgagtt tgtttgtctt attttttaatt tctcaggggc cagccagagc aggtttgttg    120
gcagtcgtac acctccgagt agtcacgcga ccagccaatg tcctggcggc gctacgggga    180
ggcggccgct cggagccag aggcggcggc ggcccggggc caccttaaga gcgcgtcgca     240
gcctggggag gctcccggca ccgagaccaa tggagctcct cctctgtttt aaatagactt    300
gcagtgtcaa tcatcttctt cttcgtcagc ctcccttcca ccgccatatt gggcaactaa    360
aaaaggaggg gggctgcttt tgggtgtttt ccccctcgtc ccttgtccca ctcactcgcg    420
gctccgagac tgggcggcgg caaggtttgg agagggctg gttcgcggga cacacgctcg     480
ccccagccta cgctccgact gtttgccacc tcctcctgcc cctcccctc ccttcccgc      540 cctccagtac acttgatcac tgaagcctcg agctgcgcgg cggctggggt gtccctgcgc    600
ctctcttccc cagacctgcg cgctactgcg gctcgggcgg tcgctcgcct ggctctgctc    660
catttgactg tctgtgtgca gtcgcagaac ttcgaagagg gttttgcgct ccatccgtgg    720
cgtttcgctt tgttcggtt tgttgtttta tttcattttt tttttttccgg agagaggcga    780 ggcggtggtc cacacccgcc cgaggaggaa gatg                                814

<210> SEQ ID NO 5
<211> LENGTH: 14
<212> TYPE: DNA
<213> ORGANISM: Homo sapiens

<400> SEQUENCE: 5
gatctcgagc ccgg                                                        14

<210> SEQ ID NO 6
<211> LENGTH: 14
<212> TYPE: DNA
<213> ORGANISM: Homo sapiens

<400> SEQUENCE: 6
ccgggctcga gatc                                                        14

<210> SEQ ID NO 7
<211> LENGTH: 1711
<212> TYPE: DNA
<213> ORGANISM: Homo sapiens

<400> SEQUENCE: 7
ccacggtgct caagcccaca ctgagagaga aatttccagc tgcaaaaggg agaagagaaa      60
cgctggaata ctagtatcgg acgttaggac atggttgtgg tgttttaaaa atcatttcat     120
catctggagt ttgaccccga ggggagtatt ttcacccttc agccctctga aagcattcac    180
tagcatctga atattgttct gagtttgttg gagcagtgaa atctggtgag agagaagggt    240
ggaggaagga aggagctgtt gtatttggcg gctggactca ggtagaggaa actgctacaa    300

-continued

| | |
|---|---|
| tcccgggaaa gaacagaaaa gtagaaaggg acgagttccc acacgcagcc aatgtccatg | 360 |
| gccttaactg tgcttgggaa ggaagatcct gggccagggg tgtaccctcg tttttcaaaa | 420 |
| actaaacgtg tctgagacag ctacaaagtt tattaaggga cttgagagac tagagttttt | 480 |
| tgttttttt ttttaatctt gagttccttt cttattttca ttgagggaga gcttgagttc | 540 |
| atgataagtg ccgcgtctac tcctggctaa tttctaaaag aaagacgttc gctttggctt | 600 |
| cttccctagg cccccagcct ccccagggat ggcagaaact tctggttaa ggctgagcga | 660 |
| accattgccc actgcctcca ccagccccca gcaaaggcac gccggcgggg gggcgcccag | 720 |
| ccccccagc aaacgctccg cggcctcccc cgcagaccac gaggtggggg ccgctgggga | 780 |
| gggccgagct gggggcagct cgccacccg gctcctagcg agctgccggc gaccttcgcg | 840 |
| gtcctctggt ccaggtcccg gcttcccggg agaggagcgg gagggaggtc ggggcttagg | 900 |
| cgccgctgcg aacccgccaa cgcagcgccg ggccccgaac ctcaggcccc gccccaggtt | 960 |
| cccggccgtt tggctagttt gtttgtctta atttaatt ctccgaggcc agccagagca | 1020 |
| ggtttgttgg cagcagtacc cctccagcag tcacgcgacc agccaatctc ccggcggcgc | 1080 |
| tcggggaggc ggcgcgctcg ggaacgaggg gaggtggcgg aaccgcgccg gggccaccttt | 1140 |
| aaggccgcgc tcgccagcct cggcggggcg gctcccgccg ccgcaaccaa tggatctcct | 1200 |
| cctctgttta aatagactcg ccgtgtcaat cattttcttc ttcgtcagcc tcccttccac | 1260 |
| cgccatattg ggccactaaa aaaaggggc tcgtcttttc ggggtgtttt tctcccctc | 1320 |
| ccctgtcccc gcttgctcac ggctctgcga ctccgacgcc ggcaaggttt ggagagcggc | 1380 |
| tgggttcgcg ggaccgcggg cttgcacccg cccagactcg gacgggcttt gccaccctct | 1440 |
| ccgcttgcct ggtccctct cctctccgcc ctcccgctcg ccagtccatt tgatcagcgg | 1500 |
| agactcggcg gccgggccgg ggcttccccg cagcccctgc gcgctcctag agctcgggcc | 1560 |
| gtggctcgtc ggggtctgtg tcttttggct ccgagggcag tcgctgggct tccgagaggg | 1620 |
| ggttcgggcc gcgtaggggc gctttgtttt gttcggtttt gtttttttga gagtgcgaga | 1680 |
| gaggcggtcg tgcagacccg ggagaaagat g | 1711 |

<210> SEQ ID NO 8
<211> LENGTH: 792
<212> TYPE: DNA
<213> ORGANISM: Homo sapiens

<400> SEQUENCE: 8

| | |
|---|---|
| acgcagcgcc gggccccgaa cctcaggccc cgccccaggt tcccggccgt ttggctagtt | 60 |
| tgtttgtctt aattttaatt ctccgaggc cagccagagc aggtttgttg gcagcagtac | 120 |
| ccctccagca gtcacgcgac cagccaatct cccggcggcg ctcggggagg cggcgcgctc | 180 |
| gggaacgagg ggaggtggcg gaaccgcgcc ggggccacct taaggccgcg ctcgccagcc | 240 |
| tcggcggggc ggctcccgcc ccgcaaccaa atggatctcc tcctctgttt aaatagactc | 300 |
| gccgtgtcaa tcattttctt cttcgtcagc ctcccttcca ccgccatatt gggccactaa | 360 |
| aaaaaggggg ctcgtctttt cggggtgttt ttctcccct cccctgtccc cgcttgctca | 420 |
| cggctctgcg actccgacgc cggcaaggtt tggagagcgg ctgggttcgc gggaccgcgg | 480 |
| gcttgcaccc gcccagactc ggacgggctt tgccaccctc tccgcttgcc tggtcccctc | 540 |
| tcctctccgc cctcccgctc gccagtccat ttgatcagcg gagactcggc ggccgggccg | 600 |
| ggcttcccc gcagcccctg cgcgctccta gagctcgggc cgtggctcgt cggggtctgt | 660 |
| gtcttttggc tccgagggca gtcgctgggc ttccgagagg gggttcgggc cgcgtagggg | 720 |

-continued

```
cgctttgttt tgttcggttt tgtttttttg agagtgcgag agaggcggtc gtgcagaccc     780
gggagaaaga tg                                                         792
```